(12) United States Patent
Herskovic

(10) Patent No.: US 11,420,074 B2
(45) Date of Patent: Aug. 23, 2022

(54) SYSTEM FOR DETECTING STENT SLIPPAGE

(71) Applicant: Arnold M. Herskovic, Chicago, IL (US)

(72) Inventor: Arnold M. Herskovic, Chicago, IL (US)

(73) Assignee: Arnold M. Herskovic, Chicago, IL (US)

( * ) Notice: Subject to any disclaimer, the term of this patent is extended or adjusted under 35 U.S.C. 154(b) by 262 days.

(21) Appl. No.: 16/819,560

(22) Filed: Mar. 16, 2020

(65) Prior Publication Data

US 2020/0289846 A1 Sep. 17, 2020

Related U.S. Application Data

(63) Continuation of application No. 15/518,648, filed as application No. PCT/US2015/058589 on Nov. 2, 2015, now Pat. No. 10,589,126.

(60) Provisional application No. 62/074,224, filed on Nov. 3, 2014.

(51) Int. Cl.
*A61N 5/10* (2006.01)
*A61B 5/06* (2006.01)
*A61B 90/00* (2016.01)

(52) U.S. Cl.
CPC ............ *A61N 5/1001* (2013.01); *A61B 5/066* (2013.01); *A61N 5/1017* (2013.01); *A61B 2090/0436* (2016.02); *A61N 5/1048* (2013.01)

(58) Field of Classification Search
CPC .. A61N 5/103–1084; A61N 2005/1085–1098; A61N 5/10–1084
See application file for complete search history.

(56) References Cited

U.S. PATENT DOCUMENTS

| | | | |
|---|---|---|---|
| 4,181,859 A * | 1/1980 | Vitalini | G03B 42/047 378/164 |
| 4,572,197 A | 2/1986 | Moore et al. | |
| 5,052,035 A * | 9/1991 | Krupnick | A61B 6/08 378/162 |

(Continued)

OTHER PUBLICATIONS

Sung et al., "Safety and efficacy of radioactive seed localization with I-125 prior to lumpectomy and/or excisional biopsy," European Journal of Radiology 82 (2013), p. 1453-1457, (Year: 2013).

*Primary Examiner* — Thaddeus B Cox
(74) *Attorney, Agent, or Firm* — Cherskov Flaynik & Gurda, LLC

(57) ABSTRACT

The invention provides a method for locating radioactive material implanted in a living body, the method having the steps of implanting a stent into the body, the stent containing the radioactive material; imaging the body to determine a first position of the stent relative to remote points on the body; determining a second position of the stent at a second time later than the time of the implanting step; and measuring the distance between said first position and said second position. Also provided is a system for determining movement of a radiation source implanted in a living body, the device having a radiographic film overlaying a region of the body so as to oppose the radiation source, whereby the film is positioned relative to a reference point on the body; a grid disposed between the film and the body; and a radio-opaque substrate overlaying the film.

9 Claims, 5 Drawing Sheets

(56) References Cited

U.S. PATENT DOCUMENTS

| | | | |
|---|---|---|---|
| 5,561,698 A * | 10/1996 | Mick | A61B 6/583 |
| | | | 378/207 |
| 6,471,632 B1 | 10/2002 | Jahrmarkt | |
| 7,853,311 B1 | 12/2010 | Webb | |
| 2004/0102699 A1 * | 5/2004 | Fors | A61B 6/502 |
| | | | 600/426 |
| 2007/0019790 A1 * | 1/2007 | Lewis | G03F 7/025 |
| | | | 378/163 |
| 2007/0075277 A1 * | 4/2007 | Smith | G21F 3/02 |
| | | | 250/515.1 |
| 2010/0127181 A1 | 5/2010 | Lovoi et al. | |
| 2011/0207987 A1 * | 8/2011 | DiCarlo | A61N 5/1017 |
| | | | 600/3 |
| 2012/0037807 A1 | 2/2012 | Ujhazy et al. | |
| 2015/0375012 A1 | 12/2015 | Herskovic | |

* cited by examiner

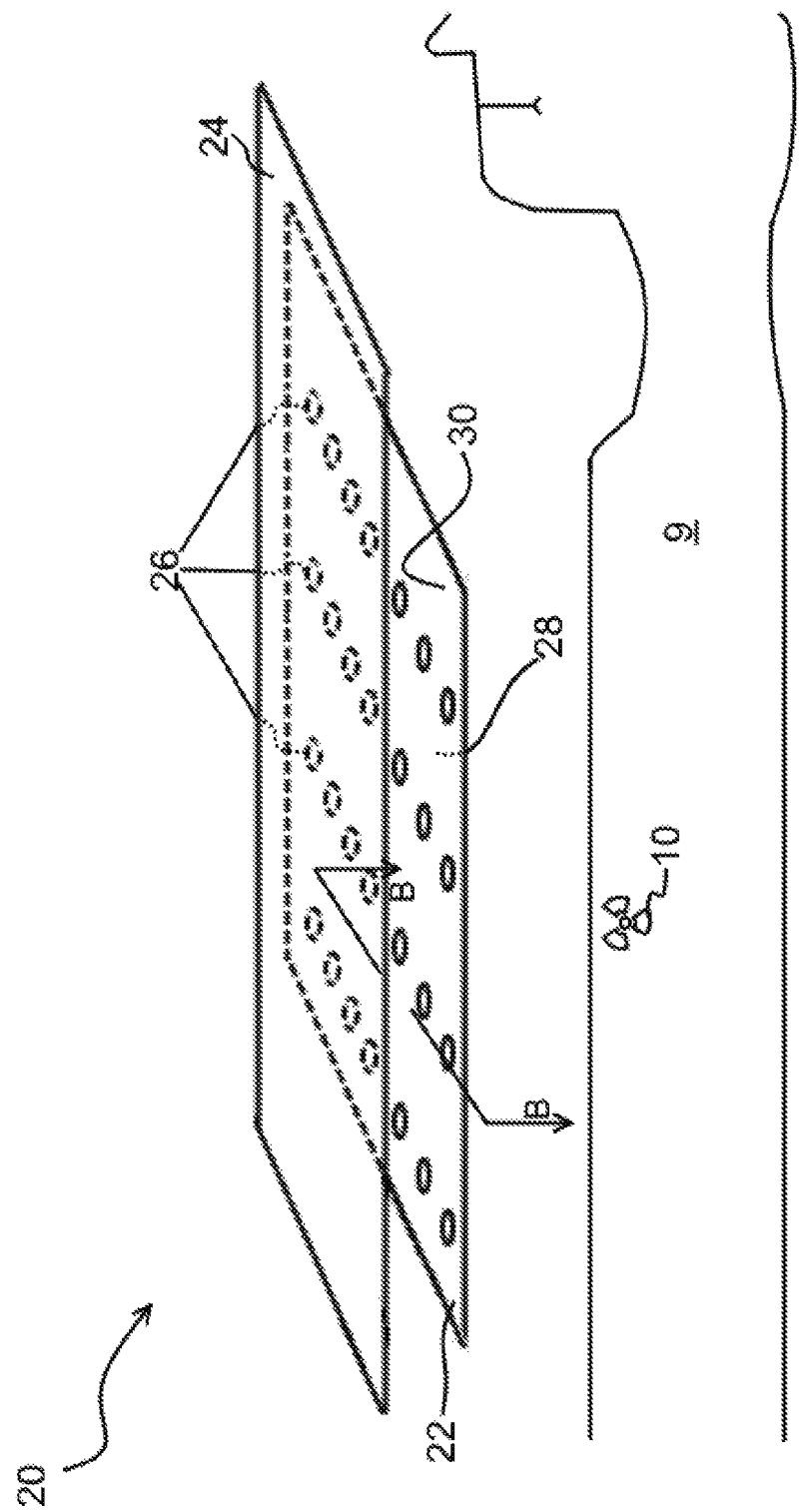

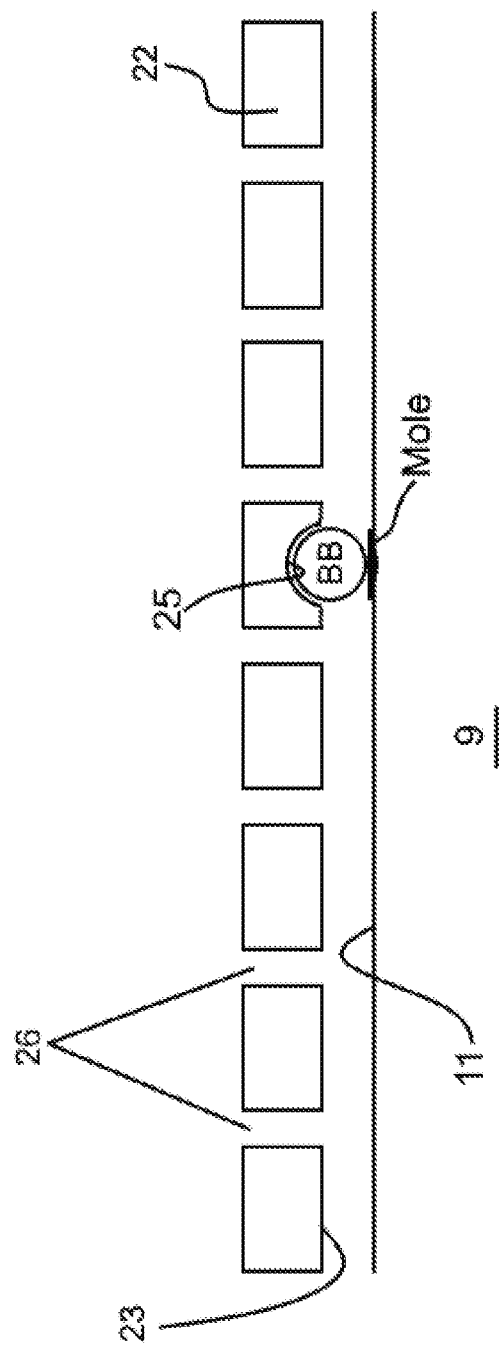

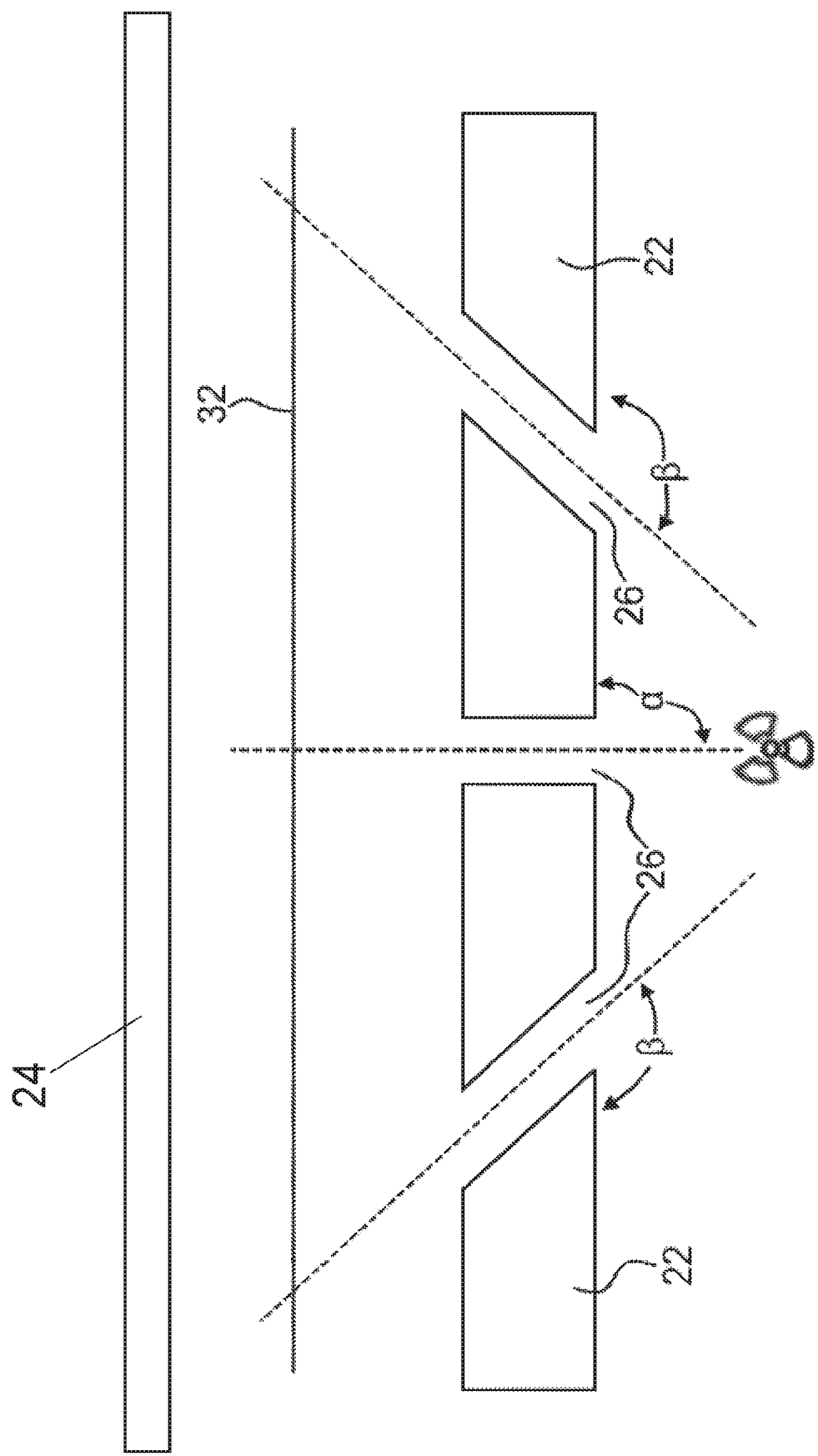

SYSTEM FOR DETECTING STENT SLIPPAGE

PRIORITY

This application claims the benefits of priority as a continuation of U.S. Non-Provisional patent application Ser. No. 15/518,648, filed on Apr. 12, 2017, now U.S. Pat. No. 10,589,126, which in turn claimed priority benefit as the nationalization of international application PCT/US2015/58589, filed on Nov. 2, 2015, which in turn claimed priority benefit of U.S. Provisional Patent Application No. 62/074,224, filed on Nov. 3, 2014, both of which are incorporated by reference in their entirety herein.

BACKGROUND OF THE INVENTION

1. Field of the Invention

This invention relates to stent slippage detection, and more specifically this invention relates to a system and method for determining, in situ, slippage of radioactive stents used to treat malignant and nonmalignant diseases.

2. Background of the Invention

Some cancers and neoplasms are easier to treat with radiation than others. Hard-to-reach neoplasms, such as those in the esophagus, intestines and other lumens, are often treated via Brachytherapy so as to minimize radiation to adjacent, healthy tissue.

Brachytherapy delivers radiation to small tissue volumes while limiting exposure of healthy tissue. In this regard, the delivered radiation conforms more to the target than any other form of radiation, (including proton therapy) as less normal, transient tissue is treated. It features placement of radiation sources, such as small radioactive particles or needles, near or within the target tissue, thus having the advantage over External Beam Radiation Therapy (EBRT) of being more focalized and less damaging to surrounding healthy tissue.

Brachytherapy is a common treatment for esophageal, prostate, and other cancers. Approximately 15,000 and 480,000 cases of esophageal cancer are diagnosed in the U.S. and worldwide, respectively. At least 50 percent of patients fail locally who present with curable cancers, which is to say that 50 percent suffer from persistence or recurrence of the cancers at the original cancer site. Another 50 percent of patients require dysphagia palliation.

Brachytherapy can be delivered in several rates: a High-Dose Rate (HDR), a Low-Dose Rate (LDR), and a very Low Dose Rate vLDR. The rates are expressed in Grays (Gy/hour) which are SI units of energy absorbed from ionizing radiation, equal to the absorption of one joule of radiation energy by one kilogram of matter.

LDR is an implant in which the tumor receives continuous radiation dose at about 8-12 Gy per day. Since the inception of brachytherapy at the beginning of the $20^{th}$ century (i.e., soon after the discovery of radiation) delivery has been predominately LDR. Therefore, much of the long term data is LDR based.

Optimal dosimetry depends on the geometry of the radiation sources relative to the target to be treated. For example, if there is slippage distally down the GI tract, the delivered radiation would be suboptimal or compromised. This occurred during the phase two study of external beam radiation brachytherapy, and concurrent chemotherapy for patients with localized carcinoma of the esophagus (Radiation Therapy Oncology Group Study 9207 final report) where low dose radiation (LDR) seeds were also used as a comparison to HDR treatment. Gaspar L E, Qian C, Kocha W I, Coia L R, Herskovic A, Graham M A phase I/II study of external beam radiotherapy, brachytherapy and concurrent chemotherapy in localized cancer of the esophagus (RTOG 9207) preliminary toxicity report Int J Radiat Biol Phys 1997 February 1:37 593-9. The freely moving radiation sources within the lumen led to bad implant dosimetries, thereby increasing the risk of being ineffective or causing injury.

Stent slippage has been reported approximately 15 percent of the time. Actual slippage rates are probably higher inasmuch as not all slippages are detected. Slippage may be due to peristalsis, gravity, tumor shrinkage, and opening of the obstruction. Generally, stent drift is in the superior-inferior direction, primarily in one plane, due to gravity. However, slippage in other directions can also occur. If the sources slip past the obstruction, suboptimal conditions could result. For example, if the tumor is 5 cm in its long axis, the radioactive part of a slipping implant is also 5 cm, and there is about 2 cm of inferior slippage, then the top half of the tumor would not be adequately irradiated while healthy parts of the esophagus inferior (i.e. downstream) from the tumor may receive too much radiation. Such instances result in what is known as radiation adverse reactions. Generally, slippage of more than two centimeters is considered counterproductive. For example, this slippage, in exposing healthy esophagus parenchyma, adds an extra margin of esophageal tissue which must now be monitored for radiation-induced anomalies or burns. Depending on factors associated with gastro intestinal stents, slippage of the stents within the GI tract can occur more often than stent sites outside of the GI tract. It is anticipated that since the goal of the radiation stent is to relieve obstruction mechanically and also by tumor shrinkage, stent slippage may occur more often. Slippage of prototypical non-radiation esophageal stents probably also occurs.

Stent slippage can occur especially if an obstructive lesion or tumor is dilated, as is often the objective. Brachytherapy dosimetries directly relate to outcome; therefore, an inexpensive methodology to raise suspicion of stent slippage would be helpful. If clinically appropriate, the physician would send the patient for confirming imaging.

In summary, it would be good medical practice that the clinician know of any increased likelihood of sub optimal radiation delivery due to stent slippage as soon as possible.

A need exists in the art for a system and method to detect slippage of medically applied stents, in situ. The system and method should utilize ordinary materials and radiation detection equipment. Such an optimized system and method, as described herein, could be performed at a physician's office or other outpatient scenario, within a matter of 15-20 minutes and be able to detect slippage distances of as little as about 10 millimeters (mm). Alternatively, such a system and method, as described herein, enables the patient to detect stent slippage between doctor visits by detecting radioactive emissions that slip from underneath a radio-opaque shield, or that emanate through apertures in the shield heretofore not experiencing emanations.

SUMMARY OF INVENTION

An object of the invention is to detect slippage, in situ, of medically inserted stents that overcomes many of the drawbacks of the prior art.

Another object of the invention is to provide a system and method for detecting slippage of a stent precisely inserted in patients for treating disease. A feature of the invention is a radio-sensitive film in close spatial relationship to radio-opaque substrate. An advantage of the invention is that the film detects movement of the stent in situ while the radio-opaque substrate prevents radiation exposure to non-patients.

Yet another object of the present invention is to provide a device to detect stent slippage in radiotherapy patients while simultaneously protecting non-patients from radiation. A feature of the device is a substantially flat or non-flat radio-opaque substrate with regions forming transversely extending holes adapted to allow the passage of radioactive particles there through. Another feature of the device is a second flat radio-opaque substrate which removably overlays the first substrate. An advantage of the device is that the first substrate will facilitate detection of movement of a radioactive implant while the second substrate prevents exposure of radiation to non-patients. Aside from flat substrates, contour-shaped substrates could also be utilized whereby the shape is complimentary to the shape of the patient.

Briefly, the invention provides a method for locating radioactive material implanted in a living body, the method comprising implanting a stent into the body, the stent containing the radioactive material; imaging the body to determine a first position of the stent relative to remote points on the body; determining a second position of the stent at a second time later than the time of the implanting step; and measuring the distance between said first position and said second position. The method also determines the length of time the stent has been in the second position, and therefore the length of time the tissue proximal to the second position was exposed to radiation.

In an embodiment of this method, the step of determining the second position comprises removably positioning a first substrate to a surface of the patient which is proximal to the stent upon implantation of the stent within the patient to establish a first measurement time, wherein the first substrate is shaped to be substantially complimentary to the surface of the patient, and wherein the first substrate has regions defining apertures extending through the substrate; measuring radiation emanating from the apertures at said first measurement time to establish a first set of apertures and a second set of apertures; maintaining the positioning of the first substrate until a second measurement time; measuring radiation emanating from the first set of apertures at the second measurement time to determine any changes in the amount of radiation emanating from the first set of apertures; and comparing the radiation emanating from the first set of apertures at the second measurement time to the radiation emanating from the second set of apertures. Instead of maintaining the positioning of the substrate until a second measurement time, body markers can be utilized to reproduce placement of the substrate over the identical region of the body at which the first measurement was taken.

Alternatively, diodes on radioactivity counters such as Geiger Counters could be used to determine if the radioactive implant has slipped.

The invention also provides a system for determining movement of a radiation source implanted in a living body, the device comprising: a radiographic film overlaying a region of the body so as to oppose the radiation source, whereby the film is positioned relative to a reference point on the body; a grid disposed between the film and the body; and a radio-opaque substrate overlaying the film. The optional grid prevents stray photons, not coming directly from the stent, from passing through the detector. A myriad of ways exist for establishing the aforementioned reference points on the body, including the use of natural moles, tiny surgical scarring, tattoos, etc. Those points are subsequently overlaid with a radio-opaque substrate such as a spherical- (e.g. a "BB") or a nonspherical protuberance. For example, the "BB," representing a raised convex contact point, may be removably received by a complementarily shaped (e.g., a concave cavity in the case of a BB) formed in a region of the film-shield construct overlaying the "BB."

Aside from (or in addition to) the spherical shapes conferred by BB's, protuberances defining nonspherical shapes, such as pyramids, stars, crosses, Ts, polygons, etc., can be utilized. These other shapes confer directional positioning of the overlying shield (instead of just latitudinal positioning) as a further aid for the patient to ensure that the shield is correctly placed. As explained elsewhere in this specification, whether spherical or nonspherical protuberances are utilized, this positioning may be maintained by hook and pile fasteners, belt buckles or other body fastening means. Alternatively, if unsymmetrical protuberances are used and reversibly attached to a patient's skin, or if more than one protuberance is used and reversibly attached to a patient's skin, then repositioning of the grid, shield or films to their original placement on the patient, wherein the overlying substrate has cavities complementary to the cross section of the protuberances, will be easy to accomplish.

In summary of this point, the protuberances removably adhered to the patient's skin serves as a reminder to the patient as to where and how the overlying detection layer is to be placed. During the course of wearing the layer, the patient can self-check its position vis-a-vis the protuberance(s).

Radiation detectors such as a Geiger counters, ionization chambers, sensitive film, diodes, or combinations thereof can be used to determine the initial position of the stent and any repositioning or slippage of the stent.

BRIEF DESCRIPTION OF DRAWING

The invention together with the above and other objects and advantages will be best understood from the following detailed description of the preferred embodiment of the invention shown in the accompanying drawings, wherein:

FIG. 2A is a schematic diagram of a second system for detecting slippage of implanted stents, in accordance with features of the present invention;

FIG. 2B is a view of FIG. 2A taken along line B-B;

FIG. 3A is cutaway view of a radio-opaque substrate for use in the invented method and system, in accordance with features of the present invention.

DETAILED DESCRIPTION OF THE INVENTION

Figure 1B:
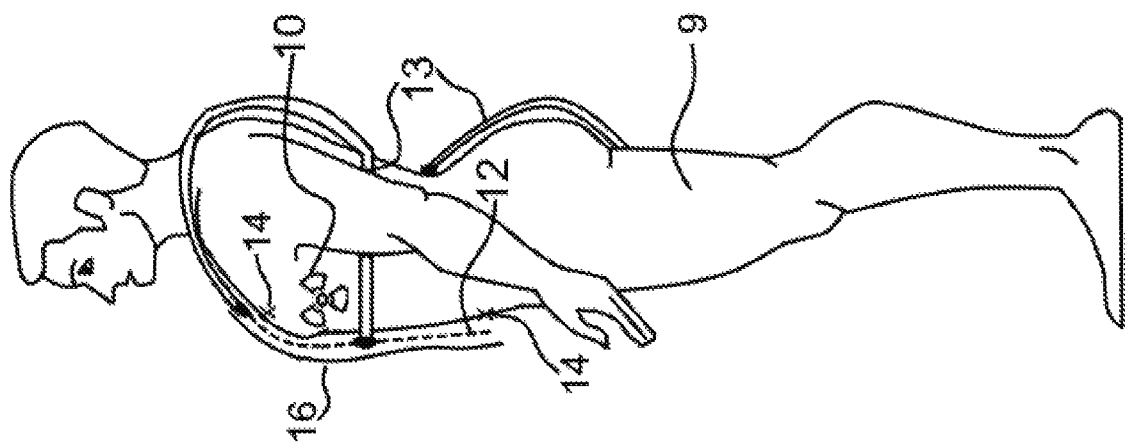
FIG. 1 is a schematic diagram of a system for detecting stents, in situ, with FIG. 1A showing an anterior view of a patient using the system and FIG. 1B which is a view of FIG. 1A along line B-B showing a left lateral view of a patient using the system, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a system and method for detecting unintended movements of brachytherapy devices such as stents in situ. The invention can detect movement in any direction, even in a retrograde direction. The invention can be utilized in combination with a means for moving a slipped stent back to its original position, or to some third position after treatment at the first position has been completed but wherein the stent inadvertently slipped from that now treated first position. An exemplary means for biasing the slipped stent to a first or third position is disclosed in applicant's International Patent Publication Number WO 2014/031950 A1, incorporated herein by reference. Specifically, a stent made of a shape memory material allows the material to be pre-programmed by thermal and/or mechanical manipulations prior to insertion such that the stent will "remember" a particular shape once inserted in situ. The stent is then deformed into a temporary shape for delivery typically by encasing it in a retractable sheath. Once the stent is released from the sheet, the stent is triggered, either naturally at ambient temperature, or by a temperature change (such as at body temperature) to return to its pre-formed final shape. This occurs because the material has a memory of its permanent shape it is given during pre-treatment at the manufacturer. The stent(s) may be inserted through a needle or trocar into the desired site.

The invention is applicable for patients being treated with or without malignancies. For example, aside from brachytherapy (which utilizes stents containing radioactive seeds) stents are also utilized to prevent benign narrowing of lumens after surgery, or benign strictures, achlasia, esophageal webs or other scarring. Further, the invention can be used in treatments for the colon, bile duct, ureter gastric outlet, bladder lumpectomies among others, depending on the different shaped radioactive stents utilized.

Stent localization to detect slippage could be accomplished with a radio frequency beacon such as Calypso or diodes, and lower cost options such as radiation counters or other electronic means. The simplicity of the instant invention makes it particularly cost effective and efficient to detect stent slippage with lower cost options, such that for example, slippage can be detected in a doctor's office with a radio activity counter such as a Geiger counter. In an embodiment of the invention, radio-sensitive film is placed in shielding material which contacts the patient. In this embodiment, a patient could wear this configuration for a period of time, then forward the configuration to a doctor or technician for determination of stent slippage. To facilitate long term wearing, the configuration includes waist, and/or leg, and/or shoulder straps terminating in hook and pile fasteners (e.g. Velcro® style fasteners), side release buckle/belt configurations or simple belt/pin-buckle configurations.

A salient feature of the invention is the use of a construct comprising radio-sensitive film in close spatial relationship with the shielding material. Suitable film is commercially available such as GAF CHROME sensitive film that can detect 0.2 cGy exposure. The film is positioned in close spatial relationship to the patient. Radiation shielding would overlay the film such that the film is between the patient and the shielding. Additionally, the shielding provides a means for enhancing film response by sequestering radiation within the confines of the film/grid/shield construct.

The film can be fitted with the shielding material via simple stitching, or removably attached (such as with a hook and pile (e.g., Velcro®) fastener.) In this second instance, the patient or a technician forwards that removably attached film to a lab and replaces it with a new one, for constant, ongoing monitoring. Optionally, self-developing films are available such that patients can be trained to remove and read the films themselves.

Since the actual patient surface dose is low, the film if used may have to be in place for days. The inventor has developed a grid pattern (such as item 11 in FIG. 1) to allow easy detection of a drift of as little as about 10 to about 30 mm. (As such, the distance between strands of the grid may be so spaced.) The grid may be reversibly attached to the film or else integrally molded therewith. During initial positioning of the grid-film construct on the patient, openings defining portions of the grid are aligned so as to be directly over the location of the radiation source. Initial radiation amounts are measured for those openings. Subsequently, slippage is determined when the film is later read for streaking or tracking from those initial apertures which results if slippage occurs. The grid allows for calculation of the distance in slippage.

Figure 1A:
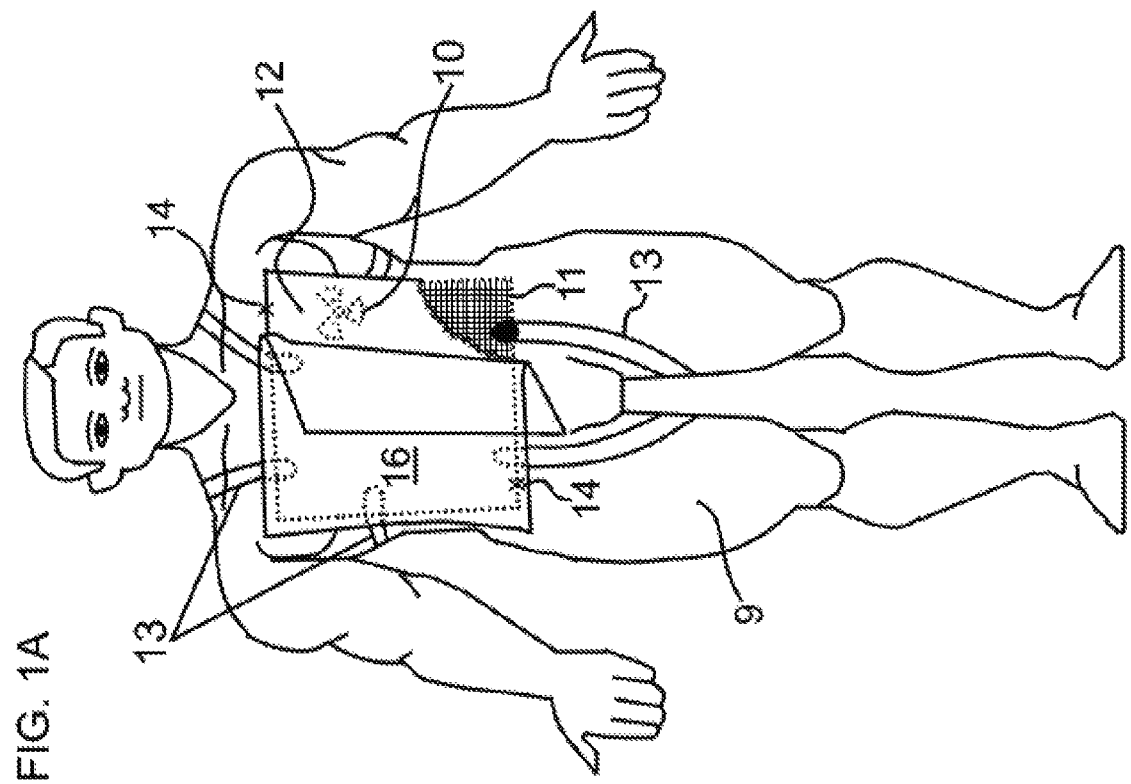

As noted supra, a myriad of fastening means can be used to attach the stent slippage system to the patient. FIGS. 1A and 1B depict one such means comprising a strap 13 or plurality of straps. A first end of a strap may terminate in one element of a hook and fastener pair, while a region of the grid 11, film or perforated substrate 22 defines the other element of the hook and fastener pair. Aside from hook and fastener (e.g. Velcro®) configurations, clasps, belts-pin-buckles, strap and slide configurations, and other infinitely adjustable, reversibly attachment means can be utilized.

FIGS. 1A and 1B shows the strap 13 encircling the trunk of the patient so that both ends of the strap attach to opposing edges of the grid, film or perforated substrate. However, a distal end of the strap can also terminate on region of the wearer's clothing. For example, if a region of the grid comprises a pile of a hook and pile fastener configuration, then the complementary end of the strap to mate with that region of the grid would define a pile. The distal end of that same strap may similarly interact with a person's clothing. Alternatively, that distal end may terminate in a belt-buckle arrangement, strap and slide configuration, or some other means for adjusting the length of the strap.

As such, the invention provides two means for detecting stent slippage (i.e., displacement), even before the patient has any symptoms.

Geiger Counter Detail

The expected radiation coming from the patient (in both HDR and LDR scenarios) would be very low, such as VLDR, which is approximately 0.2 to 0.01 Gy/hour. The internal scatter blurs the treatment edges, therefore confounding these localizations, in addition to decreasing the overall radiations. Other chambers may be more sensitive. If the radiation emanating from the patient is too low, (e.g., below approximately 8 cGy/day), then the patient donning a more radio sensitive film for a number of days may be required. These films may be very sensitive to light and may need to be enclosed in a light shielding cassette. The patient would then wear these very sensitive films for a time necessary to increase exposure time of the film to the hourly dose. For example, the wearer may increase the hourly dose to the film a 1000-fold, if worn for six weeks, or perhaps 100 fold if only worn for 4-5 days.

In an embodiment of the invention, a micro grid is placed over the patient's chest to minimize the scattered radiation and "sharpen" the ability to determine the stent's localization. (Radio sensitive film is subsequently placed over the grid, and the shielding over the film. Alternatively, a Geiger counter is used to determine initial positioning and subsequent positioning of the implant relative to the grid) Such a grid may be necessary if the internal scatter of radiation emanating from the radioactive source produces so much scatter to make localization of the stent difficult. The grid is similar to a filter in that it allows the direct radiation coming from the stent to pass through to the film while filtering out secondary emanations from other tissues. A marker on the original stent center could be placed on the patient. In an embodiment of the invention, a radiopaque substrate, such as a BB, is placed over an indelible skin marking (e.g. at tattoo), the later of which is located over the center of the radiation in the stent. The original position of the center of the radiation stent is determined via initial CT imaging of the implant performed for the routine dosimetry.

The grid could be made of most metals and/or high density materials and have a finite thickness. For example, lead, bismuth and aluminum can be used. Approximately 4 mm lead thicknesses can reduce the anticipated emitted radiation by 100 times. The low energy x rays emitted from the implant travel in many directions, further giving off many secondary interactions which also do travel in many directions. Clinical studies show that in breast implant scenarios, the significant other relative (e.g. spouse) receives about 10 millisievert (mSv) of radiation from the implant. (In the SI system, a millisievert is defined as the average accumulated background radiation dose to an individual for 1 year, exclusive of radon, in the United States.) As such, the aforementioned lead thickness as applied herein reduces exposure to the nonpatient significant other to approximately 0.1 mSv. Aside from lead or aluminum, bismuth could be utilized as a shielding metal, whereby the bismuth may be embedded in silicone.

The grid allows those primary radiations coming directly from the radiation stent to impinge on the film and not the secondaries (due to their slightly lower energies). In an embodiment of the invention, the grid is about 1 cm thick, comprised of aluminum.

Because of the low energy used during these treatment scenarios, a vest comprising a grid/film/shield or comprising just a film/shield, could be constructed of a myriad of materials. For example, for a typical implant, lead shielding for 10 times the half life value of isotopes would be only about 0.6 mm thick.

Scenario 1

A patient goes home with a radiation stent. He sees his gastro-enterologist, radiation or medical oncologist afterwards and is asymptomatic of any stent slippage. (Initially, upon stent insertion, the patient has the doses checked via a radiation plan protocol. This checking may consist of a CT image of the treated area and tattooing a reference point onto the skin of the patient in direct registration with the location of the implanted stent.)

In an embodiment of the invention, a scan of the radiation being emitted from the patient is performed using a "Geiger" counter in conjunction with a radio-opaque marker (such as a BB or other geometric sized material) placed at the reference point. For example, the BB could be positioned over a marked tattooed center projection of the radiation stent. Optionally, a filter grid or shield is placed over the patient if necessary.

After a period of time, the clinician would detect the radiation treatment volume which should coincide with the radiation plan as already performed. If there are deviations from that anticipated volume, and/or if the patient has any symptoms related to slippage, appropriate imaging such as with Computerized Tomography may be conducted to confirm stent location.

Scenario 2

The patient wears a vest defining a first patient-contacting surface and a second opposite facing surface, wherein the vest may act to decrease exposure to non-patients of emitted radiations. It would be possible to place very radiosensitive film within such a vest that could have a filter grid on the first side (i.e., the side facing the patient) and some shielding material overlaying the second side to decrease background and emitted radiations to the environment. The construct would be fairly thin (e.g., the entire vest, including grid, film and shielding would be between about 2 mm and about 10 mm thick).

The patient wears the device which is configured so that the film is in the same position relative to the patient for however long required (e.g., 4+ days (100 hours), 6 weeks (1000 hours), etc.) for radiation emanating from the stent to register on the film. These two time periods are merely illustrative such that depending on the location of the stent to the exterior of the body and the strength of the radiation source, wear times can vary from about 24 hours to about 2400 hours. For stents placed for benign situations, the relatively longer times discussed here may be needed as there will likely be less radiation involved. To aid in maintaining position of the film, a mark or plurality of marks on the patient's body would lie in registration with corresponding marks or crosshairs on the substrate containing the film.

After the stent has been implanted for a period of time, the radiosensitive film is examined for any stent slippage. Stent slippage could be shown on the film as a streak, whereby a first end of the streak represents a stent's initial location at implantation and a second end of the streak represents the stent's final location after slippage. The direction of the streak corresponds to the direction of the slippage. Also, specific qualities of the streak as empirically determined (density, thickness, contour) would enable the radiation oncologist to determine or estimate the actual dose that the tumor received.

If slippage is suspected based on this preliminary reading, then the patient would have further localization studies done, based on common clinical measures such as orthogonal imaging and/or CT. For example, the slippage in the GI tract would mostly be in a single plane, therefore a single planar measurement should be sufficient. However, other plane measurements may be required, depending on stent location and disease type.

FIG. 1A-B depicts an embodiment of a system for detecting stent slippage. FIG. 1A is an anterior view of a patient 9, within which is implanted a radiation source 10. A radiographic film 12 overlays the patient 9 and positioned on the patient using one or a plurality of remote points of reference 14. Suitable points of reference include, but are not limited to semi indelible markings made on the patient's skin, or topographical points, such as skeletal prominences on the patient's body. Exemplary points of reference may be radio-opaque substrates, such as the aforementioned BBs attached onto the skin of the patient, or subcutaneously. As discussed elsewhere in this specification, an embodiment of the invented system includes straps 13 for removably positioning and securing the film to the patient.

Overlying the film 12 is a shielding substrate 16. Suitable shielding substrate can be clothing containing lead, aluminized boron, bismuth, and combinations thereof.

Optionally, a locator grid 11, as described supra, is first placed against the patient. The grid is subsequently overlaid with the film 12. In this instance, the straps 13 can be used to secure the grid 11 to the patient. As can be seen in FIG. 1B, a proximal end of a strap 13 is attached to a depending edge of the grid 11, while a distal end of the strap is passed between the legs of the patient and up the back of the patient so as to be attached to a region of the patient's skin via a removably attached bandage, or the patient's clothing, or to the top edge of the grid.

FIG. 2A is another embodiment of a system for detecting stent slippage. This second embodiment, designated as numeral 20, comprises a first generally flat, radio-opaque substrate 22. Preferably, the shape of the substrate is somewhat complementary to an exterior body surface of the patient which is proximal to the region in which the implant resides. Portions of the first substrate define transverse apertures 26 extending through the entire thickness of the first substrate. These apertures provide a means for radiation (from an implanted stent) to emanate through the first substrate. Depending on the location of the apertures or windows relative to the stent, some of the apertures will register higher amounts of radiation than other apertures. A first surface 28 of the first substrate 22 is in contact with a patient 9, while a second surface 30 of the substrate faces outwardly from the patient. As described supra, straps 13 or other fastening means may be utilized to removably secure the first substrate 22 to the patient.

In an embodiment of the invention, the first substrate 22 is adapted to removably receive a second, similarly shaped radio-opaque substrate 24. However, this second substrate does not define apertures or other means for facilitating fluid communication or radiation emanation from the implant.

In operation, the first substrate is positioned on a patient such that it overlays a region of the patient containing a radioactive implant. This substrate is removably attached to the patient and its position precisely determined on the patient via its registration with existing or new skin tattoos, natural skin blemishes (moles, freckles, scars) and the like.

Upon precise placement of the first substrate, a first determination is made as from which apertures 26 of the first substrate emanate relatively high amounts of radiation from the implant. The determination, conducted using a radiation detector such as a Geiger counter, ionization chamber, sensitive film, diodes and combinations thereof, will establish a first location of the stent immediately after implant.

After this determination is made, the first substrate 24 is overlayed with the second substrate 24. This overlayment will prevent any emanating radiation through the apertures of the first substrate from contacting or otherwise effecting non-patients or other entities exterior of the patient 9. Optionally, the side of the second substrate opposing the exterior or second surface 30 of the first substrate 22 is coated with a radiosensitive film.

During the course of wearing this two substrate device, and as noted supra, the implanted radioactive stent 10 is subjected to peristalsis and other physiological movements. The stent is also subjected to gravity. After a predetermined time, the patient returns to his practitioner to determine if the same holes of the first substrate 22 are still emanating the majority of radiation. Specifically, the second substrate 24 is removed from the first substrate and an aforementioned means of radiation detection is applied to the apertures.

If the same holes register proportionately the same amount of radiation, then the stent has not slipped. Conversely, if different holes, either superior to, inferior from, or laterally- or medially-disposed of the first high proportion holes, now emanate high radiation, perhaps higher than the different holes emanated on the first determination, then the practitioner has an indication that the stent has moved.

The optionally featured film on the underside of the second substrate 24 may also contain tracks of the slipping stent and may provide a means for determining the direction of slippage and perhaps a time when slippage started, stopped, etc. As discussed supra, straps 13 or other fastening means can be utilized to reversibly secure the film to the patient. The film, so secured, may be a discreet component, or it may be removably attached to another substrate, or it may be integrally molded with another substrate.

Dimensions of the device 20 will vary, depending on the size of the radioactive part of the implant, on patient's size, and on the location of the implanted stent. For illustrative purposes here, the inventor envisions dimensions of approximately 10 cm to approximately 15 cm in length and approximately 5 cm to approximately 10 cm in width. Through empirical study, the holes are designed to decrease scatter of the radiation and to shield out much of the scattered radiation so as to not emanate into the immediate environment. In an embodiment of the invention, the holes through the first substrate 22 are all of the same diameter length and orientation, for example all of the apertures extend through the substrate at a 90 degree angle from either surface of the substrate.

In another embodiment of the invention, the holes are slanted so as to focus or collect emanating radiation to one spot on a radio-sensitive film 32 sandwiched between the first substrate and the second substrate 24. This embodiment is depicted in FIG. 3A. As discussed supra, the substrate 22 is positioned on top of the patient and over the radiation source 10. The substrate has apertures 26 configured at various angles $\alpha$, $\beta$ to the plane of the substrate 22 defined by the surface of the substrate contacting the patient. The angles are determined so as to optimize radiation exposure to the overlaying radio-sensitive film 32. The angles can vary from approximately 0 degrees ($\alpha$) to approximately 45 degrees ($\beta$) relative to the longitudinal axes of the apertures.

Figure 3B:
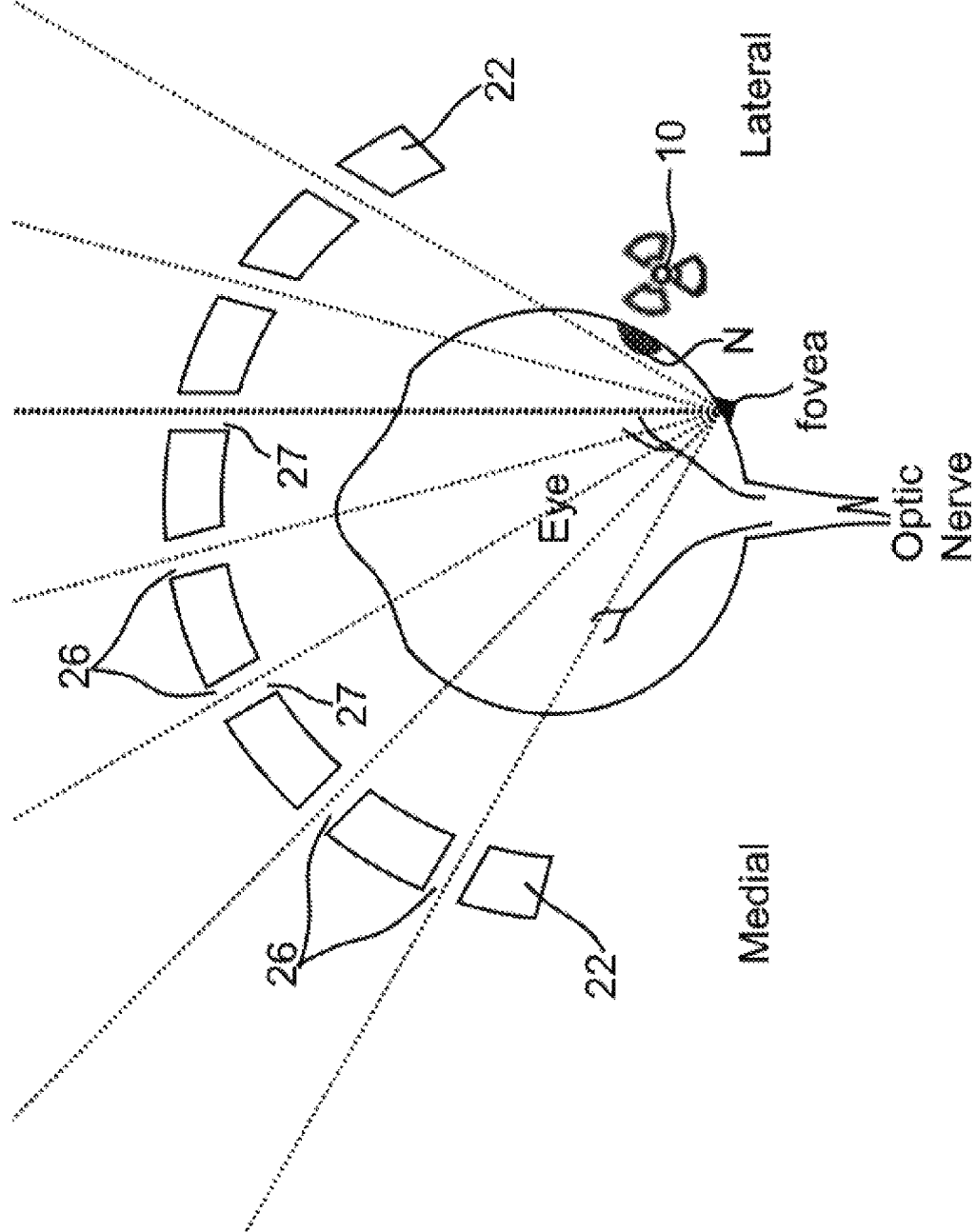
FIG. 3B is a cutaway view of a radio-opaque substrate for use in treatment of ocular maladies, in accordance with features of the present invention.

The configuration depicted in FIG. 3B may be particularly relevant when dealing with treatment of ocular melanoma, breast cancer, kidney metastasis, liver metastasis, or other maladies wherein the affected parenchyma is spherically shaped. In such instances, the substrate 22 would be concave in shape, such that the concave side faces the spherically shaped tissue, such as an eye and the radiation source. In eye treatment scenarios, for example, the stent 10 is sown into the parenchyma of the eye. Vision is conferred via the apertures 26. The apertures ensure continual vision is experienced by the wearer.

Optionally, and as depicted in FIG. 3B the proximal ends 27 of the apertures 26 (i.e., those ends closest to the radiation source) are positioned so as to converge on the fovea, or to a point in the back of the eye most sensitive for vision. The dashed lines in FIG. 3B depict the line of sight of light from regions of the environment external from the substrate 22 to the fovea.

FIG. 3B further depicts the radiation plaque or source 10 sown into the parenchyma defining the socket of the eye. In direct opposition of the radiation source 10 is a neoplasm "N" such as a typical choroidal melanoma or other type of cancers.

In another embodiment of the invention, the patient need not constantly wear the sheet defining the apertures. Rather, the examining physician first positions the sheet defining apertures to determine initial radiation levels emanating from various apertures. This first position is precisely determined on the patient using various marking means, such as a naturally occurring mole, indelible ink, or topographical changes to the skin (such as a BB, or a plurality of BBs matingly received by a concave region(s) of the first sheet 22. FIG. 2B depicts such a configuration. A downwardly directed surface 23 of the first sheet 23 defines concave regions 25 to matingly receive the BB. The BB rests on a region of the skin 11 of the patient, whereby the region 11 is easily ascertainable as a mole, a scar, tattoo or other means. In an embodiment of the invention, a region of the patient's skin directly overlying the implant is chosen for placement of at least one of the protuberances. As such, a temporary tattoo or tiny surgical scar marks that region over which the protuberance would rest.

As discussed supra, when nonspherical protrusions are used, instead of BBs, the corresponding mating cavity in the overlaying substrate would have a similar cross section area to those protrusions so as to matingly receive those protrusions. Regardless of their geometric shape, the protrusions serve as a reminder to the patient to relocate a slipped shield.

After this initial fitting, the first sheet defining apertures is replaced with the second sheet, this one not containing apertures. Again, this second solid sheet serves as a means for prevent radiation exposure to third parties. The patient then leaves.

After a predetermined time, the patient returns, and the examining physician replaces the second solid sheet with the first sheet defining apertures, taking care that the first sheet is reapplied at the first position on the patient. Then, the physician determines any changes in radiation levels emanating from the apertures of the first sheet. Depending on those changes, the physician can determine which way, and how much the stent has relocated in the patient. Depending on the presence of stent movement, or the type of movement, this process may be repeated for as long as the stent remains in the patient.

While the figures herein depict the first and second sheet as generally flat (so to accommodate abdominal and thoracic maladies such as pancreatic and biliary neoplasms), a myriad of shapes and sizes are envisioned, with the shapes and sizes dependent upon the patient surface to be covered. For example, prostate stents may require sheet configurations that are substantially nonflat, but perhaps form fitting to the supra pubic or groin area. Similarly, stents to breast tissue may require substantially concave shaped sheets, similar to the ocular substrates discussed supra.

Where non-flat substrates are utilized, 3D mapping and subsequent printing of the sheets may be in order to assure custom fit of the sheets to the relevant patient surface.

Radiation Source
And Vehicle Detail

A myriad of stent configurations and sources are suitable and commercially available. The choice of stent and of source is an empirical one, and based on patient malady or situation. For example, the radioactive material may comprise a radioactive isotope selected from the group consisting of $^{125}$I, $^{103}$Pd, $^{169}$Yb, $^{131}$Cs, $^{99}$Mo, $^{225}$Ac, $^{213}$Bi, $^{211}$At, $^{89}$Sr, $^{90}$Y, $^{131}$I, $^{133}$Xe and combinations thereof. However, the isotope list in this paragraph is illustrative only. The invented system is applicable to any isotope which can be utilized for human or nonhuman implantation.

Stent configurations can vary widely. For example, an interior surface of the stent can be lined with said radioactive material. The stent may encapsulate the radioactive material. Or the radioactive material may coat an outside surface of a stent or other vehicle so as to be supported by the vehicle.

Exemplary stent configurations and radiation source types and detail are found in International Patent Application Publication Number WO 2014/031950 A1, the entirety of which is incorporated by reference.

Radio Opaque
Substrate Detail

A first aperture defining shield substrate comprising lead is utilized. As discussed supra, a second shield without apertures, may overlay the first shield. Lighter substrates, while also radio opaque, would embody greater thicknesses. Another embodiment of the invention utilizes just a single sheet of shielding in conjunction with the grid as featured in FIG. 1. The grid would provide the means to locate the implant if the implant slipped so as to be misaligned with the shield.

Shield dimensions are empirically determined. Generally, shields or grids can be square, rectangular, ovoid, polygonal, etc., and range from between approximately 4 cm wide to 10 cm wide and from about 6 cm to about 20 cm long and shaped to substantially fully contact a patient's abdomen and/or thorax. Inasmuch as no abdomen is standard in size or topography, 3D tomography and 3D printing may be utilized. Shapes will vary if instead of a patient's abdomen, or similarly flat dorsal surface such as the small of the patient's back, a patient's neck, breast, groin, or underarm area is to be overlaid and monitored. The substrates would be radio opaque, and be comprised of lead, aluminum, bismuth, or some other metal. Lighter substrates, while also radio opaque, would embody greater thicknesses.

Thicknesses will vary, depending on metal type. For example, given a ¹⁄₁₀₀ attenuation goal, lead-based shields would be thinner compared to aluminum-based shields. The tenth half value layer (hvl) of lead (Pb) is 0.6 mm, while for aluminum it is 1.8 mm. This compares to the 1.7 cm hvl of living tissue. Pb density is 11.3 g/cc and Al density is 7 g/cc. In an embodiment of the invention, a typical shield would measure 8 cm×15 cm or approximately 120 square centimeters. Given a ¹⁄₁₀₀th attenuation goal, approximately 0.12 cm lead thickness is required, bringing the total weight of the lead shield with these dimensions to approximately 162 grams or 6 ounces. If aluminum is utilized, a 0.4 cm thickness is required, bringing the total weight to approximately 336 gm or about 11 to 12 oz.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A system for determining movement of a radiation source implanted in a living body over time, the system comprising:
   a) a radiographic film configured to overlay a region of the living body so as to oppose the radiation source, whereby the film is configured to be positioned relative to a reference point on the living body;
   b) a grid configured to be disposed between the film and the living body wherein the film is integrally molded with the grid; and
   c) a radio-opaque substrate overlaying the film.

2. The system as recited in claim 1 wherein the film is reversibly attached to the radio-opaque substrate.

3. The system as recited in claim 1 further comprising:
   a radiation detecting device configured to be positioned relative to the reference point.

4. The system as recited in claim 3 wherein the radiation detecting device is a radioactivity counter.

5. The system as recited in claim 4 wherein the radioactivity counter is selected from the group consisting of a Geiger counter, a diode, and combinations thereof.

6. The system as recited in claim 4 wherein the reference point is positioned over the radiation source.

7. The system as recited in claim 6 wherein radio-opaque substrate is configured to be placed over the reference point.

8. The system as recited in claim 7 wherein the radio-opaque substrate is a BB.

9. The system as recited in claim 1 wherein the reference point is a tattoo.

* * * * *